US012405199B2

(12) United States Patent
Lim et al.

(10) Patent No.: US 12,405,199 B2
(45) Date of Patent: Sep. 2, 2025

(54) METHOD AND SYSTEM FOR MONITORING A QUALITY OF PEPPER POWDER

(71) Applicant: KOREA FOOD RESEARCH INSTITUTE, Jeollabuk-do (KR)

(72) Inventors: Jeong-ho Lim, Jeonju-si (KR); Kee-jai Park, Seongnam-si (KR); Gyeongsik Ok, Hwaseong-si (KR); Jeongseok Cho, Daegu (KR); Dae-Yong Yun, Gwangju (KR); Seul-Ki Park, Busan (KR); Gyuseok Lee, Daegu (KR); Jeong Hee Choi, Yongin-si (KR); Kyung-Hyung Ku, Seoul (KR); Sangseop Kim, Jeonju-si (KR); Jihyun Lee, Seoul (KR); Hahyeong Yu, Anseong-si (KR); Ji-Young Choi, Gwangju (KR)

(73) Assignee: KOREA FOOD RESEARCH INSTITUTE, Wanju-gun (KR)

( * ) Notice: Subject to any disclaimer, the term of this patent is extended or adjusted under 35 U.S.C. 154(b) by 237 days.

(21) Appl. No.: 18/466,306

(22) Filed: Sep. 13, 2023

(65) Prior Publication Data

US 2024/0337574 A1    Oct. 10, 2024

(30) Foreign Application Priority Data

Apr. 5, 2023    (KR) ........................ 10-2023-0044596

(51) Int. Cl.
*G01N 5/00*       (2006.01)
*G01N 15/0205*    (2024.01)
(Continued)

(52) U.S. Cl.
CPC ....... *G01N 15/0205* (2013.01); *G01N 33/025* (2013.01); *G01J 3/2823* (2013.01); *G01N 2015/1029* (2024.01)

(58) Field of Classification Search
CPC ............. G01N 15/0205; G01N 33/025; G01N 2015/1029; G01J 3/2823
See application file for complete search history.

(56) References Cited

U.S. PATENT DOCUMENTS 10,473,585 B2 *   11/2019   Coffey ............... G01N 15/0205
2011/0218739 A1 *  9/2011   Mo ........................ G01N 21/85
                                                              702/23

FOREIGN PATENT DOCUMENTS

| CN | 106226267 A | 12/2016 |
| CN | 109984207 A | 7/2019  |

(Continued)

OTHER PUBLICATIONS

Ji-Young Choi et al.; "Effect of Moisture Content Difference on the Analysis of Quality Attributes of Red Pepper (*Capsicum annuum* L.) Powder Using a Hyperspectral System"; Foods 2022, 11, 4086., published on Dec. 17, 2022.—full translation from USPTO (Year: 2022).*

(Continued)

*Primary Examiner* — Rebecca C Bryant
(74) *Attorney, Agent, or Firm* — Studebaker Brackett PLLC

(57) ABSTRACT

The present invention relates to a method for monitoring the quality of red pepper powder, comprising the steps of: estimating at least one of a first particle size and a first moisture content of a first red pepper powder, based on the spectroscopic image data of the first red pepper powder obtained in or before and after at least one of the grinding process, filtration process and sterilization process of red pepper powder; calculating a second spicy level, based on at least one of the first particle size and the first moisture content, and the spectroscopic image data; and estimating a third spicy level of a first mixed red pepper powder in the mixing process, based on at least one of the first particle size (Continued)

and the first moisture content, the second spicy level, and an input amount of the first red pepper powder.

13 Claims, 15 Drawing Sheets

(51) Int. Cl.
*G01N 33/02* (2006.01)
*G01J 3/28* (2006.01)
*G01N 15/10* (2006.01)

(56) References Cited

FOREIGN PATENT DOCUMENTS

| KR | 10-2001-0053957 A | 7/2001 |
| KR | 10-1135505 B1 | 6/2012 |

OTHER PUBLICATIONS

Bonifazi, G. et al., "Dried red chili peppers pungency assessment by Visible and Near Infrared Spectroscopy", Proc. Of SPIE, vol. 10986, pp. 109861S-1 to 109861S-12, doi: 10.1117/12.2517069, May 14, 2019.

Esquerre, C. A. et al., "Use of an NIR MEMS spectrophotometer and visible/NIR hyperspectral imaging systems to predict quality parameters of treated ground peppercorns", LWT—Food Science and Technology, vol. 131, 109761, pp. 1-8, https://doi.org/10.1016/j.lwt.2020.109761, Jun. 15, 2020.

An Office Action; "Notice of Reasons for Refusal," mailed by the Japanese Patent Office on Sep. 3, 2024, which corresponds to Japanese Patent Application No. 2023-172942 and is related to U.S. Appl. No. 18/466,306.

Ji-Young Choi et al.; "Effect of Moisture Content Difference on the Analysis of Quality Attributes of Red Pepper (*Capsicum annuum* L.) Powder Using a Hyperspectral System"; Foods 2022, 11, 4086. <https://doi.org/10.3390/foods11244086>, published on Dec. 17, 2022.

Ji-Young Choi et al.; "Grading the pungency of red pepper powder using hyperspectral imaging coupled with multivariate analysis"; Korean J Food Preserv, 29(6), 918-931 (2022), published on Oct. 31, 2022.

\* cited by examiner

METHOD AND SYSTEM FOR MONITORING A QUALITY OF PEPPER POWDER

TECHNICAL FIELD

The present invention relates to a method for monitoring the quality of red pepper powder and a system therefor, and more specifically, to a method for monitoring the quality, for example, spicy level, particle size, and the like of red pepper powder in the red pepper powder manufacturing process and a system therefor.

BACKGROUND ART

Red pepper is a single crop belonging to the family Solanaceae, and has a red color and pungency. In general, red pepper is dried and powdered to be used as a spice for food additives. Preference for the quality of red pepper is ultimately determined by the mixed taste of pungency, sweetness and flavors of other components, contained in red pepper powder. Homologs of capsaicinoid, which is a component that determine the pungency of red pepper, are capsaicin, dihydrocapsaicin, nordihydrocapsaicin, and the like.

There is a problem in that there are many varieties of these peppers, and even if they are the same variety, the content of capsaicinoids and the like is different depending on the cultivation conditions such as sunlight, precipitation and soil characteristics, or the harvest time, and thus, it is difficult to uniformly produce the taste and quality of the red pepper powder even if the red pepper powder is made from the same variety of red pepper.

Currently, the Ministry of Agriculture, Food and Rural Affairs of Korea presents criteria for standardizing the particle size of red pepper powder produced by various companies, farms and regions into three types, for example, coarse red pepper powder, medium red pepper powder and fine red pepper powder, and presents criteria for standardizing the level of spiciness into five levels. However, it is currently difficult to perform quality control in the actual manufacturing process because technology for monitoring the level of spiciness (spicy level) and particle size of red pepper powder in real time has not been implemented. Currently, in order to analyze the quality of red pepper powder, the content measurement method is used to directly measure the components after taking a sample of red pepper powder and being subject to a pre-processing process, but there is a problem in that this method is difficult to apply in the actual manufacturing process because it takes several days or at least several hours for analysis and processing. For example, the pungent component of red pepper powder may be measured for capsaicinoid content using high-performance liquid chromatography (HPLC) and gas chromatography/mass spectrometry (GC/MS). However, since this method also uses a destructive method through pre-processing of the sample, it takes a long time to confirm the analysis result.

On the other hand, a method for analyzing the quality of red pepper powder using spectroscopic images is introduced in Korean Patent No. 10-1135505. However, it is known that the accuracy of pungency measurement by spectroscopy is lowered because commercially manufactured and sold red pepper powder has particles of various sizes. Moreover, there is a problem in that accuracy is further lowered because spot analysis is used when analyzing red pepper powder using conventional spectroscopy (image). In addition, there is also a problem that the measured value of pungency is different due to the difference in moisture content according to the particle size of the red pepper powder.

DISCLOSURE

Technical Problem

In order to solve these conventional problems, it is an object of embodiments of the present invention to provide a method for monitoring the quality of red pepper powder and a system therefor, which can manufacture red pepper powder of a desired pungency by obtaining spectroscopic image data of red pepper powder in real time during the red pepper powder manufacturing process to estimate a spicy level, particle size, moisture content or the like of red pepper powder and predicting a final spicy level of a mixed red pepper powder discharged after the mixing process in the red pepper powder manufacturing process.

In addition, it is an object to provide a method for monitoring the quality of red pepper powder and a system therefor, which can manufacture red pepper powder with a desired taste or quality by estimating the quality of red pepper powder such as ASTA value and sugar content in addition to the spicy level of red pepper powder based on spectroscopic image data.

The technical problems according to the technical idea of the technology disclosed in the present specification are not limited to the above-mentioned problems, and other problems not mentioned will be clearly understood by those skilled in the art from the following description.

Technical Solution

The above objects can be achieved by a method for monitoring the quality of red pepper powder, comprising the steps of: estimating at least one of a first particle size and a first moisture content, and a first spicy level, of a first red pepper powder, based on the spectroscopic image data of the first red pepper powder obtained in or before and after at least one of the grinding process, filtration process and sterilization process of red pepper powder; calculating a second spicy level by correcting the first spicy level based on at least one of the first particle size and the first moisture content; storing data of at least one of the estimated first particle size and first moisture content, and the second spicy level in a memory; and estimating a third spicy level of a first mixed red pepper powder in the mixing process, based on the stored data and an input amount of the first red pepper powder.

In addition, the above objects can be achieved by a method for monitoring the quality of red pepper powder, comprising the steps of: estimating at least one of a first particle size and a first moisture content of a first red pepper powder, based on the spectroscopic image data of the first red pepper powder obtained in or before and after at least one of the grinding process, filtration process and sterilization process of red pepper powder; estimating a second spicy level, based on at least one of the first particle size and the first moisture content, and the spectroscopic image data; and estimating a third spicy level of a first mixed red pepper powder in the mixing process, based on at least one of the first particle size and the first moisture content, the second spicy level, and an input amount of the first red pepper powder.

In addition, the method may further comprise the step of estimating at least one of a second particle size and a second moisture content of the first mixed red pepper powder, based on at least one of the first particle size and the first moisture content, and the input amount of the red pepper powder.

In addition, the method may further comprise the step of comparing the pre-set target spicy level and target particle size of the first mixed red pepper powder with the third spicy level and the second particle size to determine at least one of the type, input amount, moisture content and grinding degree of dried red pepper to be added to the future grinding process, or to determine at least one of the spicy level, input amount, moisture content and particle size of a second red pepper powder to be added to the mixer in the future.

In addition, the method may further comprise the steps of: estimating a first sugar content of the first red pepper powder based on the spectroscopic image data; predicting a second sugar content of the first mixed red pepper powder; and comparing the second sugar content with the pre-set target sugar content of the first mixed red pepper powder to determine the type and input amount of dried red pepper to be added to the future grinding process, or to determine the sugar content and input amount of the second red pepper powder to be added to the mixer in the future.

In addition, the method may further comprise the steps of: estimating a first ASTA value of the first red pepper powder based on the spectroscopic image data; estimating a second ASTA value of the first mixed red pepper powder; and comparing the second ASTA value with the pre-set target ASTA value of the first mixed red pepper powder to determine the ASTA value and input amount of dried red pepper to be added to the future grinding process, or to determine the ASTA value and input amount of the second red pepper powder to be added to the mixer in the future.

In addition, the method may further comprise the step of generating a visualization map of the first particle size, the first moisture content, the second particle size, the second moisture content, the second spicy level, and the third spicy level.

In addition, the above objects may be achieved by a computer program stored in a non-transitory recording medium configured to perform the method for monitoring the quality of red pepper powder.

A system for monitoring the quality of red pepper powder according to one embodiment of another technical idea may comprise: one or more spectroscopic devices installed in or before and after at least one of the grinding process, filtration process and sterilization process of red pepper powder to obtain spectroscopic image data of a first red pepper powder; and a monitoring device for receiving spectroscopic image data in conjunction with the spectroscopic devices, wherein the monitoring device may be configured to perform the method monitoring the quality of red pepper powder as described above.

In addition, the spectroscopic devices may be configured to periodically or intermittently obtain spectroscopic image data of the first red pepper powder.

In addition, the monitoring device may be configured to store the estimated or determined data of the first red pepper powder, the second red pepper powder and the first mixed red pepper powder in a memory, or to send and receive the data to the control part.

Advantageous Effects

As described above, the method for monitoring the quality of red pepper powder of the present invention and the system therefor may manufacture red pepper powder of a desired pungency by obtaining spectroscopic image data of red pepper powder in real time during the red pepper powder manufacturing process to estimate a spicy level, particle size, moisture content or the like of red pepper powder and predicting a final spicy level of a mixed red pepper powder discharged after the mixing process in the red pepper powder manufacturing process based thereon.

In addition, these may manufacture red pepper powder with a desired taste or quality by estimating the quality of red pepper powder such as ASTA value and sugar content in addition to the spicy level of red pepper powder based on spectroscopic image data.

On the other hand, the effects described above are merely illustrative, and effects predicted or expected from the detailed configuration of the present invention from the viewpoint of those skilled in the art may also be added to the unique effects of the present invention.

BEST MODE

Figure 1:
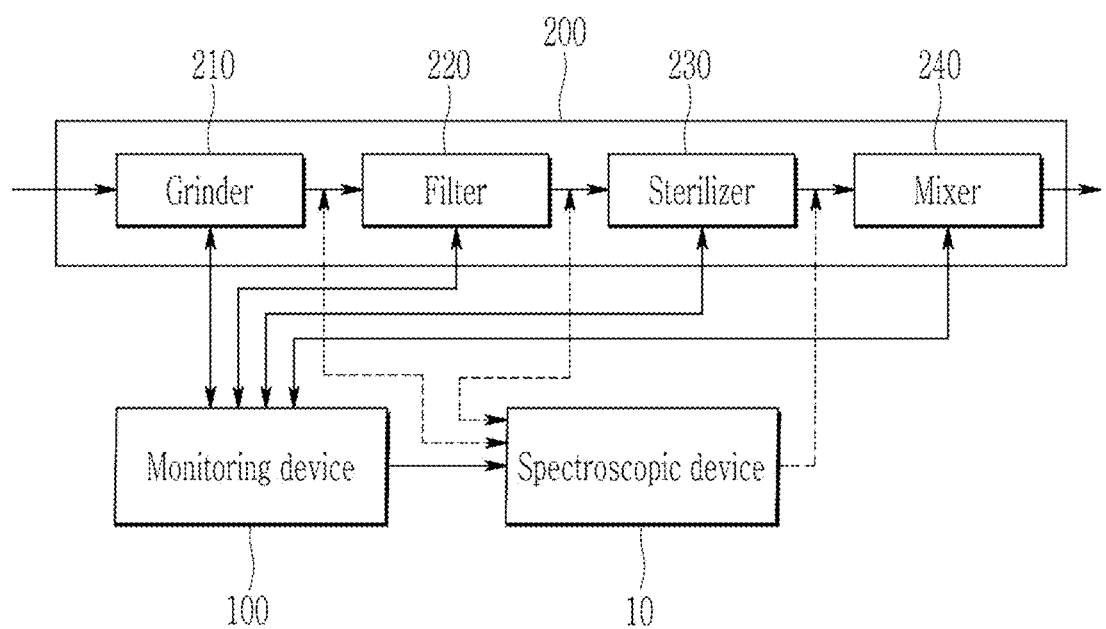
FIGS. 1 and 2 are schematic diagrams of the system for monitoring the quality of red pepper powder according to one embodiment of the present invention.

Hereinafter, one embodiment disclosed in the present specification will be described in detail with reference to the appended drawings, but the same or similar components will be given the same reference numerals regardless of the reference numerals, and duplicate descriptions thereof will be omitted. As used in the following description, the suffixes "module" and "part" for components are given or used interchangeably in consideration of ease of writing the specification, and do not have meanings or roles that are distinct from each other by themselves. In addition, in describing one embodiment disclosed in the present specification, if it is determined that the specific description of the related known technologies may unnecessarily obscure the gist of one embodiment disclosed in the present specification, the detailed description thereof will be omitted. In addition, it should be understood that the appended drawings are only for easy understanding of one embodiment disclosed in the present specification, and do not limit the technical idea disclosed in the present specification, which includes all modifications, equivalents, and substitutes included in the spirit and technical scope of the present specification.

Terms including ordinal numbers, such as first and second may be used to describe various components, but the components are not limited by the terms. The terms are only used to distinguish one component from another component.

When a component is referred to as being "coupled" or "connected" to another component, it should be understood that the component may be directly coupled or connected to the another component, but other components may be present in the middle. On the other hand, when an component is referred to as being "directly coupled" or "directly connected" to another component, it should be understood that no other component is not present in the middle.

Singular expressions include plural expressions unless the context clearly indicates otherwise.

As used herein, terms such as "comprise," "have," and the like are intended to indicate that there is a feature, number, step, operation, component, part, or combination thereof described in the specification, and it should be understood that the terms do not exclude in advance the possibility of the presence or addition of one or more other features, numbers, steps, operations, components, parts, or combinations thereof.

Although the present disclosure has been illustrated and described in detail in the drawings and the above description, it will be understood that the present disclosure is to be considered illustrative rather than restrictive in its properties, and only certain embodiments have been shown and described, and all changes and modifications that fall within the spirit of the present disclosure are preferably protected.

Figure 2:
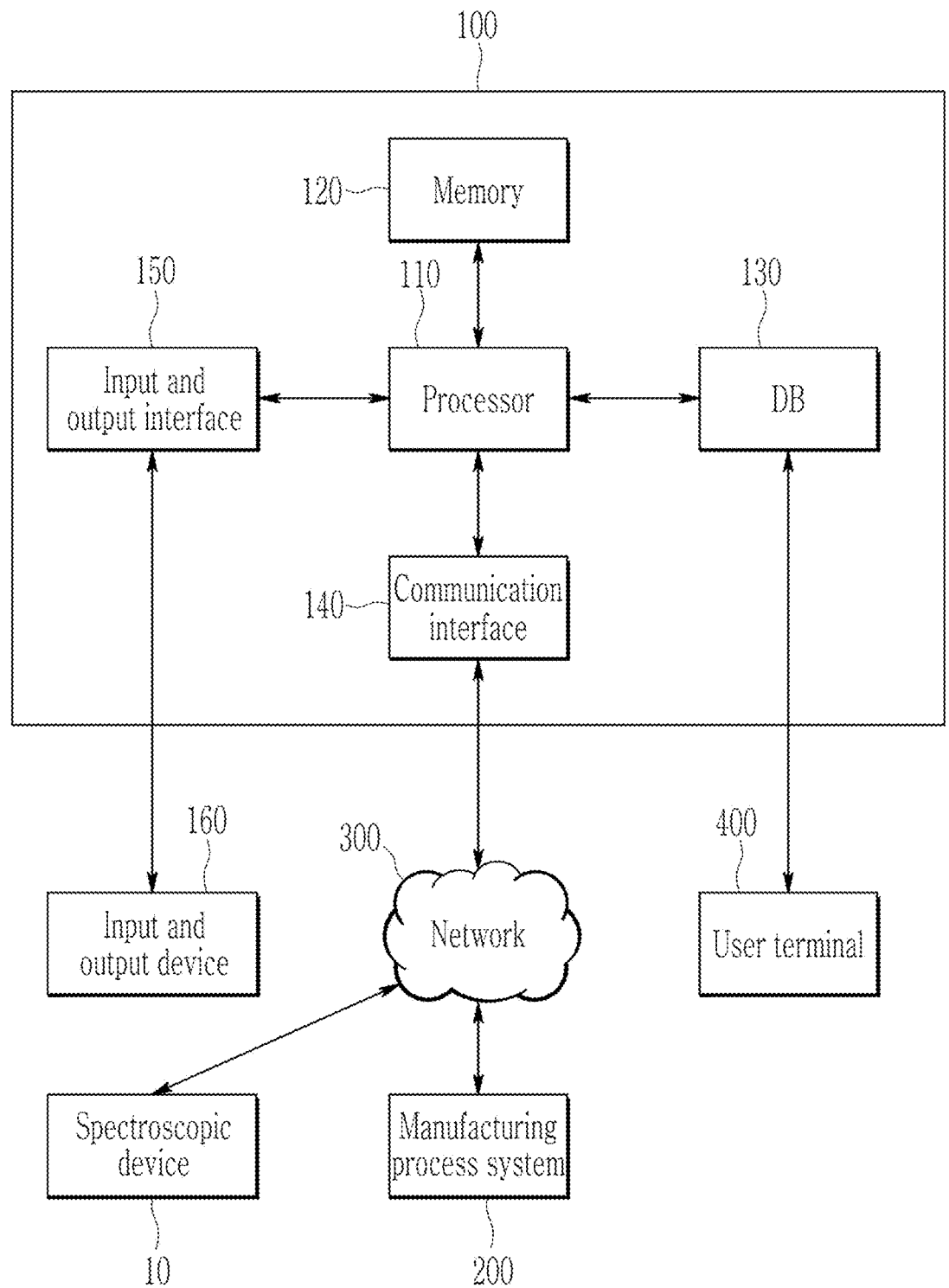

FIGS. 1 and 2 are schematic diagrams of the system for monitoring the quality of red pepper powder according to one embodiment of the present invention.

Referring to FIG. 1, the system for monitoring the quality of red pepper powder according to one embodiment of the present invention comprises: a spectroscopic device 10 installed in a red pepper powder manufacturing process system 200 to obtain spectroscopic image data of red pepper powder being manufactured; and a monitoring device 100 for monitoring the quality of red pepper powder being manufactured in conjunction with the spectroscopic device 10.

The red pepper powder manufacturing process system 200 according to one embodiment of the present invention is a process facility for manufacturing red pepper powder, and comprises grinder 210, a filter 220, a sterilizer 230, and a mixer 240.

The grinder 210 is for grinding dried red pepper into powder and is used in the grinding process. At the front end of the grinder 210, processes such as washing of dried red pepper, removal of foreign substances, drying, moisture control, crushing, and separation of seeds and pulp may be added, if necessary. The grinder 210 grinds the dried red pepper to a desired particle size through multiple steps using a roll mill.

The filter 220 is installed at the rear end of the grinder 210 to sort the ground red pepper powder into a desired particle size, and for example, may be powdered into various sizes, if necessary. Powder may be made in multiple stages in order of size from small to large, if necessary, and red pepper powder of a desired particle size may be produced by properly mixing them. For example, according to the Korean government's red pepper powder size standards, the specification standard of fine red pepper powder is less than 10% remaining on a sieve of 2.00 mm and 40% or more remaining on a sieve of 1.00 mm, and the specification standard of medium red pepper powder is less than 40% remaining on a sieve of 1.00 mm and 40% or more remaining on a sieve of 500 µm, and the specification standard of coarse red pepper powder is less than 10% remaining on a test sieve of 1.00 mm and less than 40% remaining on a test sieve of 500 µm, and thus, red pepper powder of a desired size may be produced by appropriately mixing powdered red pepper powders to meet these standards.

The sterilizer 230 is for sterilizing red pepper powder, and is installed at the rear end of the filter 220 to be used in the sterilization process. An ultraviolet sterilizer may be used as the sterilizer 230. The sterilization process may be omitted if necessary or may be arranged before but not after the filtration process.

The mixer 240 is for mixing red pepper powder, and a mixer for mixing filtered and sterilized red pepper powder may be used. If a predetermined certain amount of red pepper powder subject to the above-described series of manufacturing processes is collected, a mixing process is performed through the mixer 240.

For example, the filtered and sterilized red pepper powder is introduced into the mixer 240, and if the mixer 240 is filled with a certain amount of red pepper powder, the mixer 240 may be operated. In another embodiment, the filtered and sterilized red pepper powder is collected in a container, and if a certain amount is collected, it may be introduced into the mixer 240 to perform a mixing process. In another embodiment, red pepper powder may be produced by separately collecting the red pepper powder sorted by particle size through the filter 220, and then determining the amount of red pepper powder for each particle size corresponding to the target particle size to introduce them into the mixer 240.

On the other hand, in FIG. 1, processes such as sterilization, drying, removal of foreign substances and packaging may be further added at the rear end of the mixer 240.

The spectroscopic device 10 is for obtaining spectroscopic image data of red pepper powder, and at least one spectroscopic device may be installed in the manufacturing process of red pepper powder. For example, the spectroscopic device 10 is installed in or before and after at least one of the grinding process, filtration process and sterilization process of red pepper powder to periodically or intermittently obtain spectroscopic image data of the red pepper powder in the manufacturing process. The spectroscopic device 10 is preferably installed before the mixing process, or before or after the process after the grinding process, and in some cases may be installed in the process. For example, the spectroscopic device 10 may be installed in a connection line at the rear end of the grinder 210, a connection line at the rear end of the filter 220, a connection line at the rear end of the sterilizer 230, or the sterilizer 230.

The spectroscopic device 10 has a wired or wireless communication interface for interworking with the monitoring device 100 described below, and the spectroscopic image data obtained by the spectroscopic device 10 is transmitted to the monitoring device 100 through the communication interface. The spectroscopic device 10 may be a hyperspectral device for obtaining a reflection spectrum of a wavelength range in the range of 900-1700 nm, which is a short wave infrared (SWIR) region, and may further include a spectroscopic device 10 for obtaining images in a near-infrared region or an RGB region.

The spectroscopic device 10 may include an InGaAs sensor and two halogen light sources, and may obtain a spectroscopic image using a line scan method. The spectroscopic device 10 obtains spectroscopic image data of a region of a certain size, not spectroscopic data of a specific spot. This makes it possible to check what kind of distribution the red pepper powder is formed in a certain region rather than a certain spot.

If the surface of the red pepper powder sample is uneven, it may affect the absorbance, and thus, the spectroscopic device 10 may further include a mechanical configuration for evenly flattening the surface. In addition, a mechanical configuration for excluding the influence of the surrounding environment when obtaining a spectroscopic image may be further included. The spectroscopic device 10 may be set to periodically or intermittently obtain spectroscopic images. For example, an instruction may be transmitted to obtain a spectroscopic image once every 10 minutes, 30 minutes or 1 hour, or whenever new red pepper powder is introduced.

The monitoring device 100 is for receiving spectroscopic image data obtained by the spectroscopic device 10 in conjunction with at least one spectroscopic device 10 to analyze and monitor the quality of red pepper powder in the manufacturing process, and may be implemented by at least one computing device or computer system including a processor 110 and a memory 120 in which at least one program code and data executed in the processor 110 are stored. On the other hand, the monitoring device 100 interworks with control parts such as the manufacturing process system 200 and the user terminal 400 through the network 300, and through this, may transmit a control signal to the manufacturing process system 200, or receive an instruction from a control part such as the user terminal 400 and transmit requested data.

The processor 110 is for executing and processing computer program instructions by performing basic logic, calculation, arithmetic operation, and the like, and is executed while the computer program code stored in the memory 120 is loaded into the processor 110.

The memory 120 is a computer-readable recording medium and may include a random access memory (RAM), a read only memory (ROM), and a permanent mass storage device such as a disk drive. In addition, at least one program code executed by the processor 110 may be stored in the memory 120. These program codes may be loaded into the memory from a floppy disk drive, tape, DVD/CD-ROM drive, memory card, and the like other than the memory 120.

The monitoring device 100 may further include a DB 130, a communication interface 140 and an input and output interface 150. The DB 130 is a DB 130 related to the quality of red pepper powder, and may include cultivation environment and drying process data such as variety, production area, producer, harvest time and drying, quality data such as spectroscopic data, and the like. The communication interface 140 is for communicating with other devices, for example, the user terminal 400 for managing the processes, and the like, including the spectrometer 10, the red pepper powder manufacturing process system 200 or devices in each process (for example, grinder 210, filter 220, sterilizer 230, mixer 240, and the like), through a network, and may include, for example, any one or more networks of such as a personal area network (PAN), a local area network (LAN), a campus area network (CAN), a metropolitan area network (MAN), a wide area network (WAN), a broadband network (BBN) and the Internet. The input and output interface 150 is for interworking with the input and output device 160, and includes wired and wireless communication interfaces. The input and output device 160 may include an input device such as a microphone, keyboard or mouse, and an output device such as a display or speaker.

The monitoring device 100 (processor) analyzes periodically or intermittently received spectroscopic image data to estimate the quality of red pepper powder and stores it in the memory 120. The information stored in the memory 120 is analysis time, quality of red pepper powder, input amount (production amount) of red pepper powder corresponding to the quality, and the like. The input amount (production amount) of red pepper powder may be set or input automatically or by a user in proportion to time.

The monitoring device 100 may include a spectroscopic analysis model for estimating the quality of red pepper powder, for example, particle size, moisture content, spicy level, sugar content or ASTA value, and the like, based on spectroscopic image data. The spectroscopic analysis model may include, for example, a multivariate statistical model, and an analysis model through machine learning or deep learning, and may perform unsupervised learning or supervised learning by actually obtaining spectroscopic data of red pepper powder with various production areas, harvest times, particle sizes, and spicy levels as learning data.

The spectroscopic analysis model may be prepared by deriving the relationship between the quality factor and the spectroscopic image of red pepper powder data through multivariate statistical analysis, chemometrics modeling, and the like. The spectroscopic analysis model according to the present invention is a model that may predict quality factors such as particle size, moisture content and/or spicy level of red pepper powder based on spectroscopic image data of red pepper powder, and a partial least square regression (PLSR) statistical technique that combines principal component analysis and multiple regression analysis, and the like may be used.

In PLSR, the predicted value Y may be calculated by following equation 1:

$$Y = \beta X + b \qquad \text{[Equation 1]}$$

(where Y is the quality grade of red pepper powder, the content of a specific ingredient, particle size, moisture content, spicy level, or they like; X is spectroscopic image data; β is a vector of regression coefficients; and b is a model offset.)

The monitoring device 100 may further include a model evaluation part for evaluating the performance of the derived spectroscopic analysis model. The model evaluation part evaluates the performance of the PLSR prediction model based on the results of the PLSR model using spectroscopic image data, and the performance of the prediction model may be implemented with an evaluation program that evaluates accuracy, precision, sensitivity, specificity, F1 score, and the like.

On the one hand, the monitoring device 100 may further include a feature extraction module for extracting and classifying features from the spectroscopic image received from the spectroscopic device 10 and a preprocessing module for removing scattering effects or noise from the spectroscopic image data. The feature extraction module may be prepared by additionally extending a unique algorithm for feature extraction of red pepper powder spectroscopic images, for example, classification, and the like, in consideration of spectroscopic pattern, texture, shape, and the like, using the ENVI program and the Per Class program as software to performing image analysis such as image extraction, classification and integration. The preprocessing module is for removing the scattering effect or noise of the spectrum due to the uneven appearance of the sample or the change in the surrounding environmental conditions, and may perform preprocessing such as normalization, smoothing, standard normal variate (SNR), multi-scatter correction (MSC), Savitzky-Golay (SG) primary or secondary derivative, and may be implemented using, for example, a program such as Unscrambler.

The spectroscopic analysis model according to the present invention may estimate the quality of red pepper powder, such as particle size (for example, size of particle or particle size level), moisture content, sugar content, spicy level (for example, capsaicinoid content, level of spiciness, or the like) or ASTA value, based on the spectroscopic image data. In this case, the quality estimation value of the red pepper powder may be expressed as a certain numerical value or a level (or step) having a certain numerical range. For example, the particle size may be expressed as three levels (for example, S (fine red pepper powder, 425 μm or less), M (medium red pepper powder, 425-850 μm) and L (coarse red pepper powder, 850 μm-2 mm)), and the spicy level may be expressed as five levels (for example, "mild" (capsanoid content less than 150 mg/kg), "mild spicy" (150-300 mg/kg), "normal spicy" (300-500 mg/kg), "spicy" (500-1,000 mg/kg) and "very spicy" (more than 1,000 mg/kg), or three levels (for example, mild spicy, normal spicy and spicy).

The spectroscopic analysis model may estimate the particle size (first particle size), moisture content (first moisture content), sugar content and/or spicy level (first spicy level) through PLS-DA (discriminant analysis) analysis, based on the received SWIR spectroscopic data.

Figure 3:
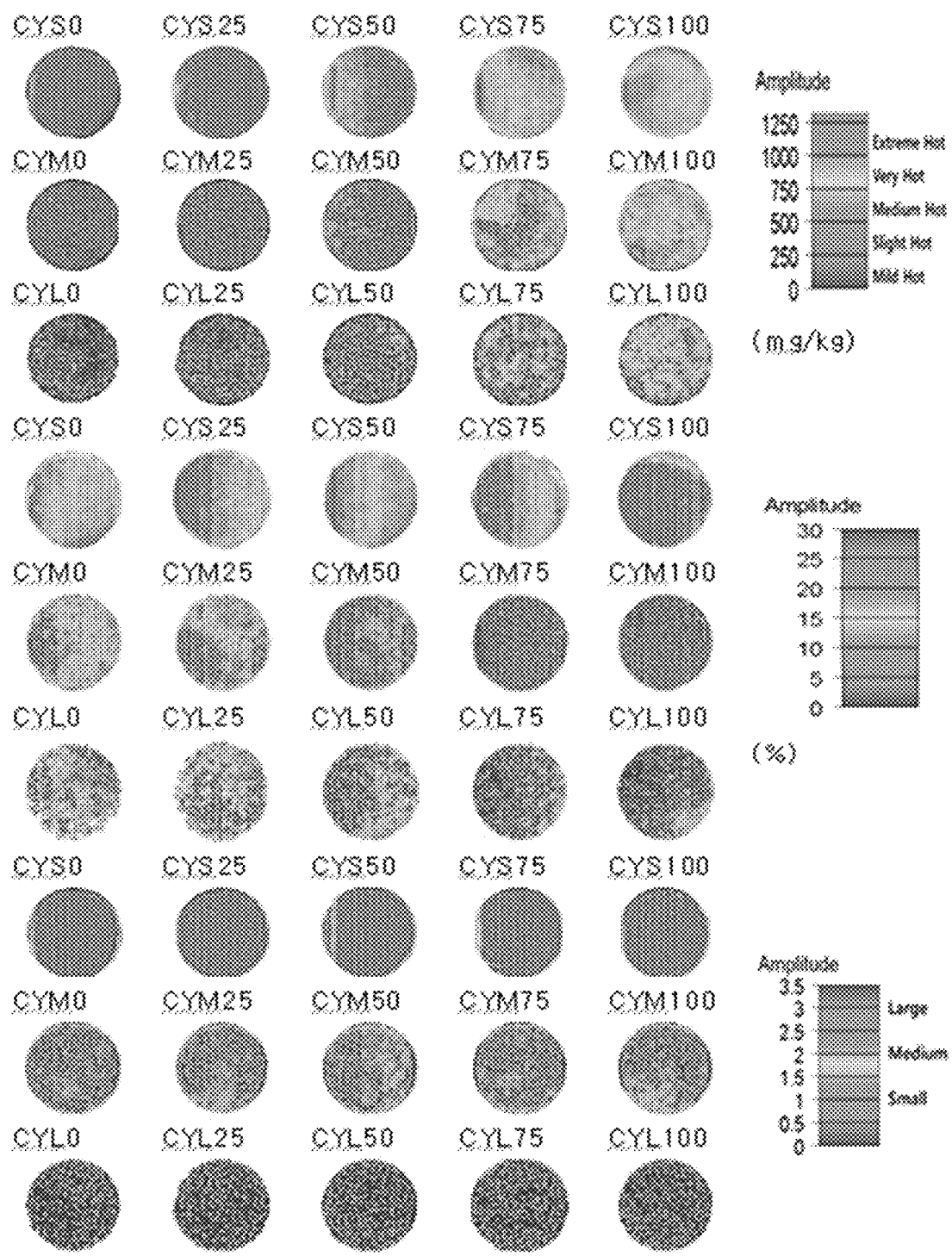
FIG. 3 is a diagram showing maps of spatially visualizing the quality of red pepper powder based on spectroscopic image data of red pepper powder analyzed by the monitoring device according to one embodiment of the present invention.

The monitoring device 100 may further include a visualization module for generating a visualization map of data on the quality of red pepper powder predicted through the spectroscopic analysis model. FIG. 3 is an example of maps of spatially visualizing the quality of red pepper powder based on spectroscopic image data of red pepper powder analyzed by the monitoring device 100 according to one embodiment of the present invention, and shows the results of visualizing the spatial distribution of spicy level (capsaicinoid content, and the like), free sugar content and particle size (size of particle). In FIG. 3, CY represents the production area of red pepper powder, respectively, -S (small, 425 μm or less), -M (medium, 425-850 μm), -L (large, 850 μm-2 mm) represent the particle size, respectively, 0, 25, 50, 75 and 100 represent the mixing ratio (i.e., level of spiciness) of Cheongyang pepper. For example, CYL25 refers to red pepper powder with a large particle size and 25% mixed Cheongyang red pepper, produced from the CY area. In the present invention, the user may intuitively confirm the quality of red pepper powder by visualizing not only the quality value but also the quality distribution and change according to the space of the red pepper powder sample.

Figure 4A:
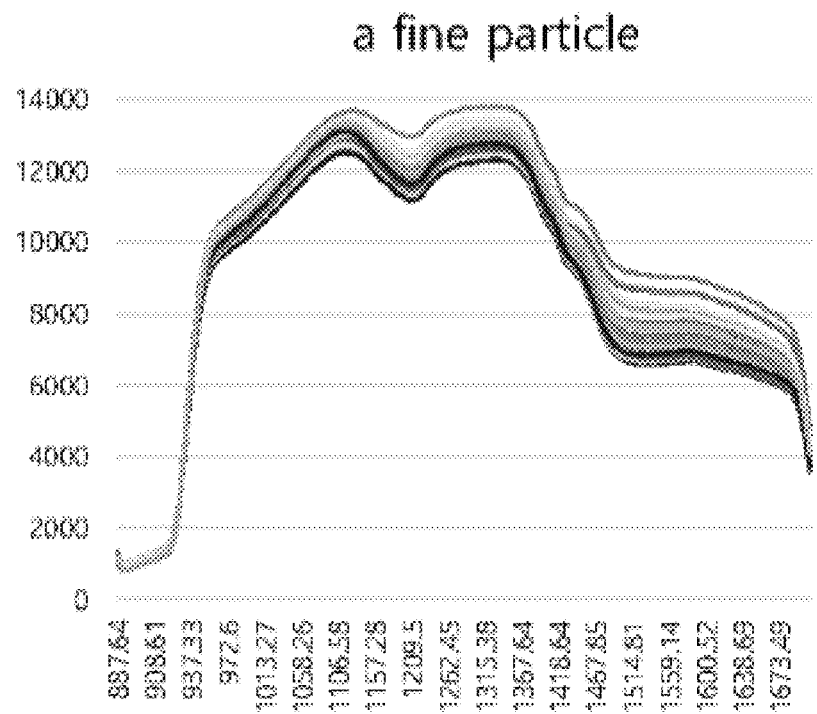
FIGS. 4A-4C show spectral spectrum distributions according to the particle size of red pepper powder analyzed by the monitoring device according to one embodiment of the present invention.
Figure 4B:
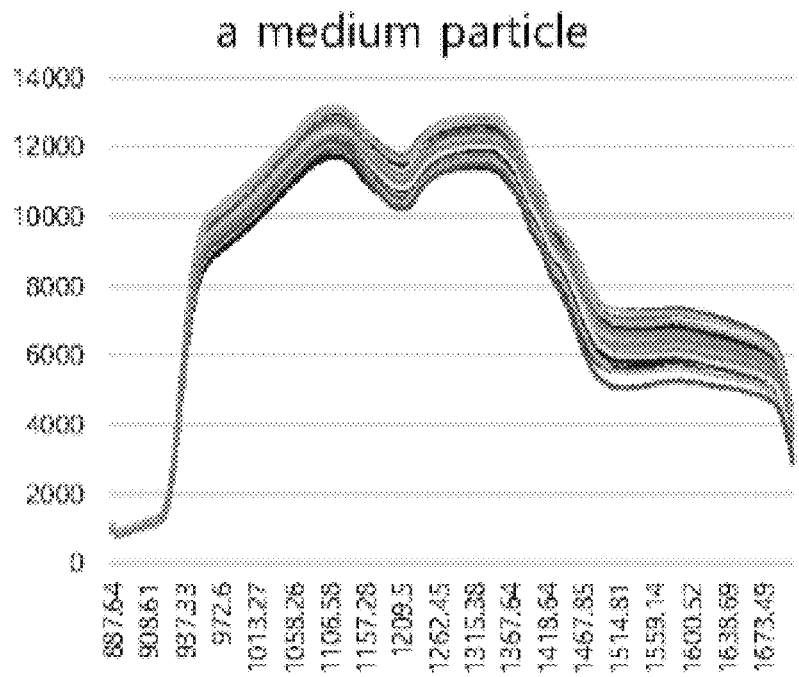
Figure 4C:
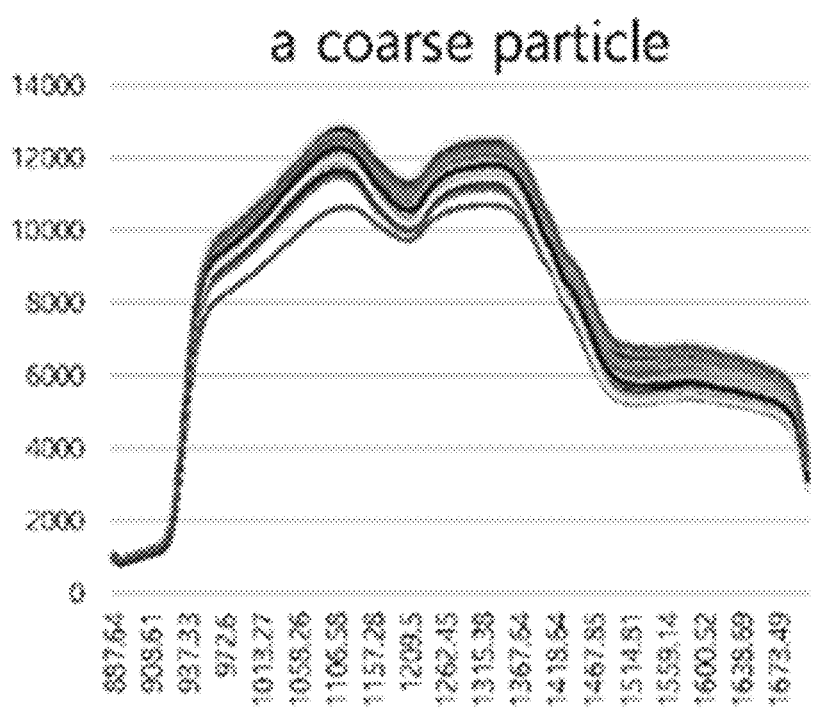

FIGS. 4A-4C show the spectral spectrum distribution according to the particle size of red pepper powder, and show the spectral spectrum results of red pepper powder each having a fine particle(S) (FIG. 4A), a medium particle (M) (FIG. 4B) and a coarse particle (L) (FIG. 4C). Referring to FIGS. 4A-4C, when the red pepper powder was a fine particle, the reflectance was remarkably high, and the variation between samples was low. On the other hand, coarser particles of red pepper powder have lower reflectance and larger data deviation.

Figure 5A:
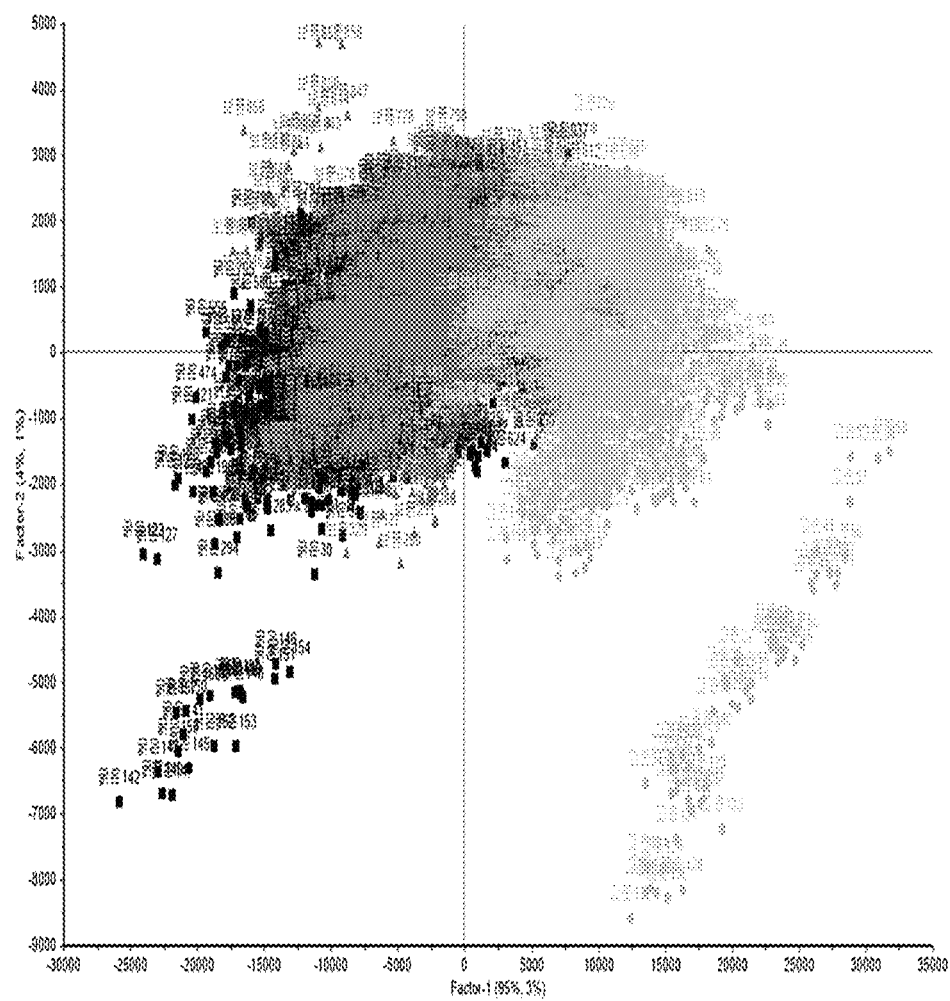
FIGS. 5A-5B are diagram showing the analytical results for discriminating the particle size of red pepper powder.
Figure 5B:
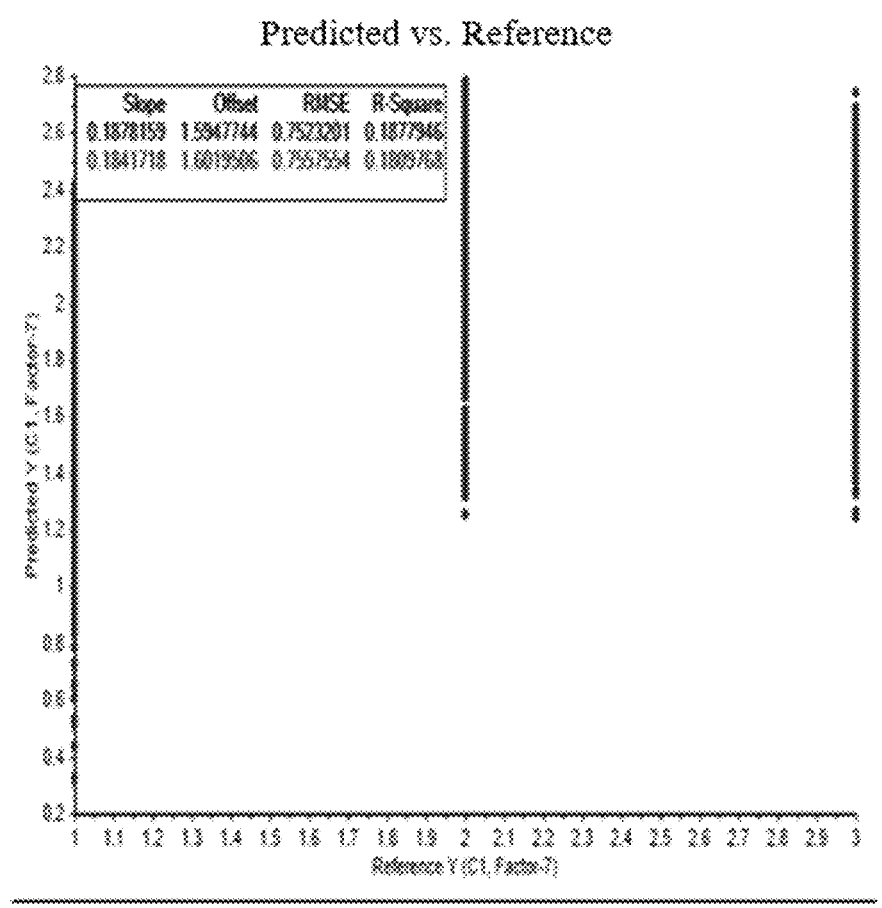

FIGS. 5A-5B show the analytical results for discriminating the particle size of red pepper powder, wherein 5A shows the PLS-DA analysis result, and 5B shows the regression coefficient of the model. Referring to FIGS. 5A-5B, fine particles (S, red), medium particles (M, green) and coarse particles (L, blue) are clearly distinguished in the PLS-DA analysis, and from these results, a model capable of estimating the particle size according to the spectral spectrum of red pepper powder may be created.

Figure 6A:
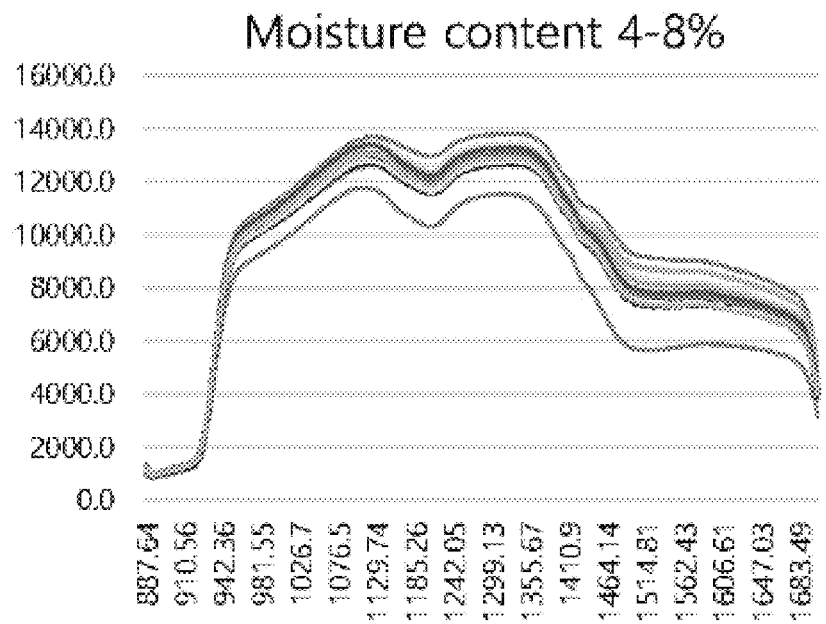
FIGS. 6A-6C show spectral spectrum distributions according to the moisture content of red pepper powder analyzed by the monitoring device according to one embodiment of the present invention.
Figure 6B:
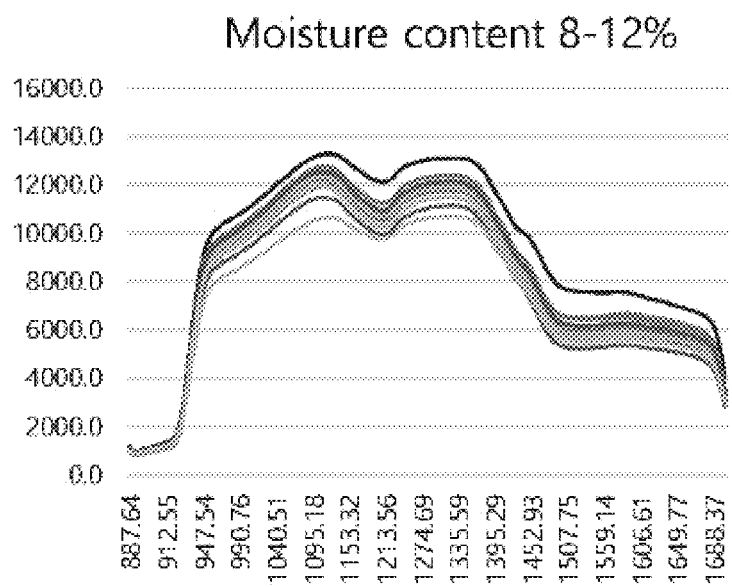
Figure 6C:
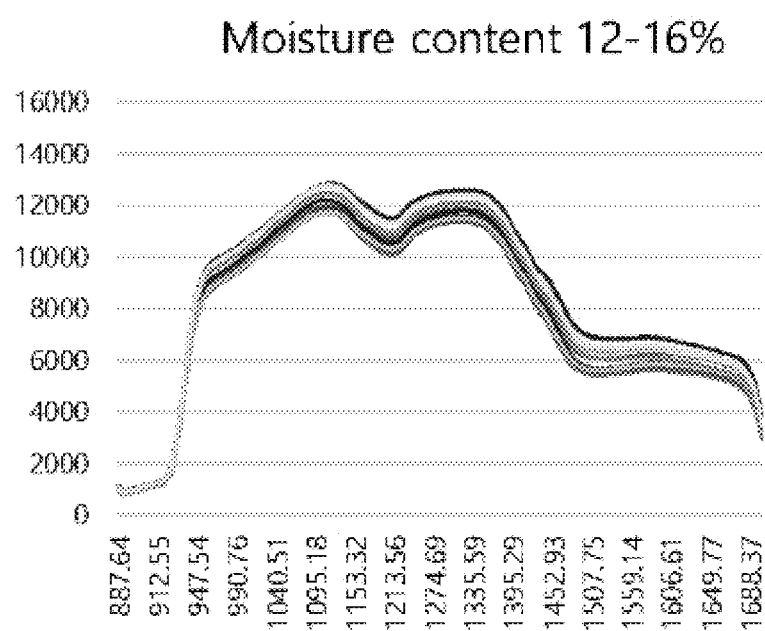
Figure 7A:
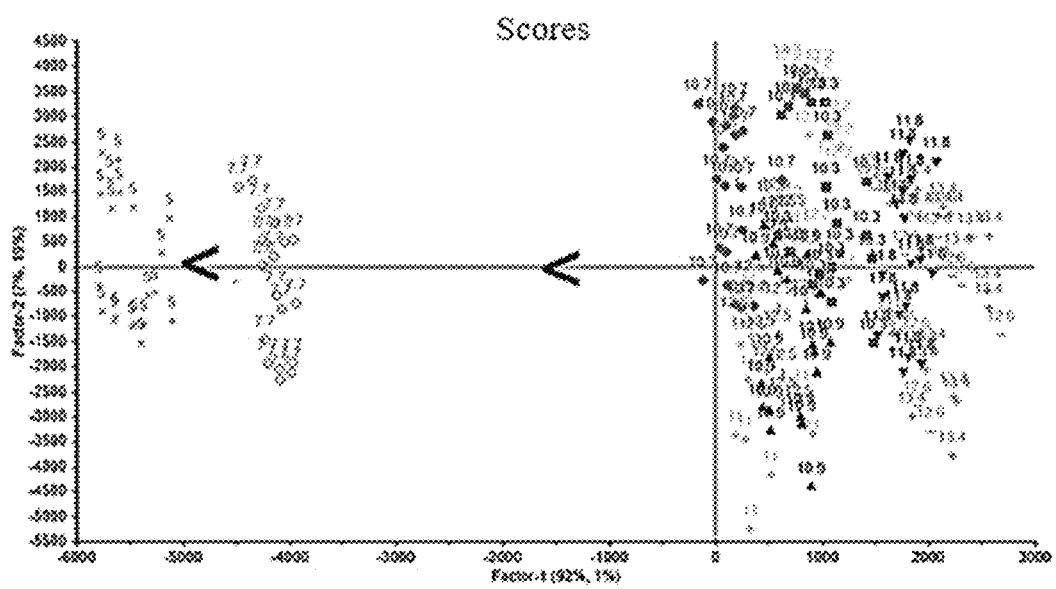
FIGS. 7A-7B are diagram showing the results of analyzing the moisture content of red pepper powder.
Figure 7B:
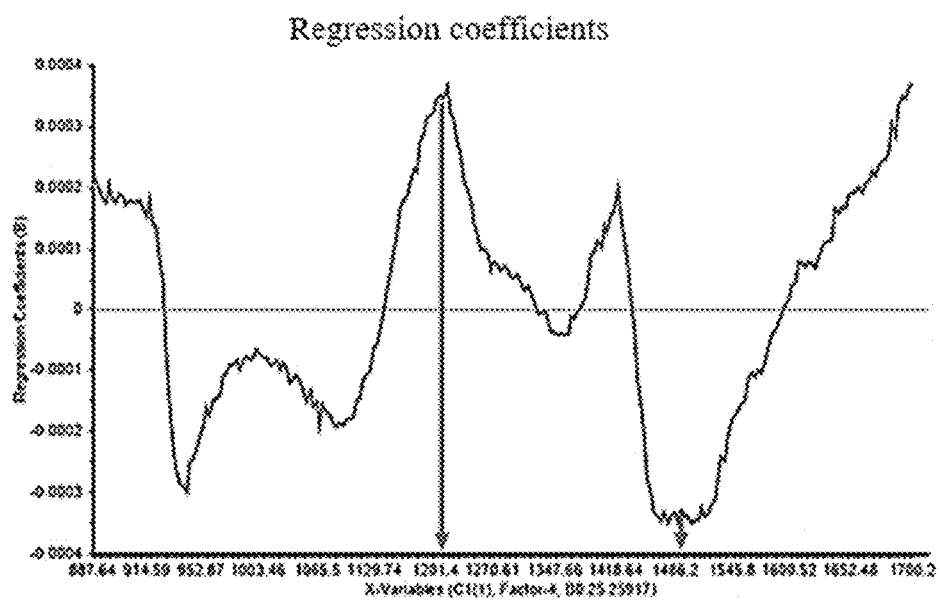

FIGS. 6A-6C show spectral spectrum distributions according to the moisture content of red pepper powder, and show the spectroscopic data of red pepper powder each having moisture content of (6A) level 1 (4-8%), (6B) level 2 (8-12%) and (6C) level 3 (12-16%); and FIGS. 7A-7B show the results of analyzing the moisture content of red pepper powder, wherein FIG. 7A shows the PLS-DA analysis result, and FIG. 7B shows the regression coefficient. Referring to FIGS. 6A-6C and 7A-7B, in the analysis of the moisture content of red pepper powder, grouping can be confirmed in the score plot, and in particular, it can be seen that the 1200 nm and 1480 nm wavelength bands show an absorption phenomenon due to the influence of O—H bonds constituting moisture. From these results, a model capable of estimating the moisture content according to the spectral spectrum of red pepper powder may be created.

The spectroscopic analysis model according to the present invention may calculate a second spicy level by estimating a first particle size and/or a first moisture content of red pepper powder based on the spectroscopic image data and correcting the first spicy level based on the first particle size and/or first moisture content.

The pungent component of red pepper powder is a capsaicinoid-based compound, and is mainly composed of capsaicin and dihydrocapsaicin, which are present in a composition ratio of 70% and 21-40%, respectively, and the sum of capsaicinoid-based compounds is referred to as total capsaicinoid in the present specification. Red pepper is largely composed of pulp, seeds, and placentas, and capsaicinoids are mainly distributed in the placenta, and thus, as the placenta, which has a relatively weak tissue, and the diaphragm to which the placenta is attached are ground first in the grinding process, the smaller the particle size of the red pepper powder, the higher the spicy level. Thus, if the mixing distribution of the particle size is different, the color or pungency of the red pepper powder is different, and thus, in the present invention, the spicy level is corrected in consideration of the particle size. When a model for estimating the spicy level is learned, it may be learned by classifying the level of spiciness according to the total capsaicinoid content into three or six levels.

Table 1 below shows the capsaicinoid content according to the mixing ratio of Cheongyang red pepper (0, 25, 50, 75 and 100(%)) and particle size (S, M and L).

TABLE 1

| | Capsaicinoid (mg/kg) | | |
|---|---|---|---|
| | Capsaicin | Dihydrocapsaicin | Total |
| CYS0 | 199.20 ± 0.52[b,] | 135.77 ± 0.65[b] | 334.97 ± 1.17[b] |
| CYS25 | 315.47 ± 9.60[de] | 167.57 ± 2.93[de] | 483.04 ± 12.41[d] |

TABLE 1-continued

| | Capsaicinoid (mg/kg) | | |
|---|---|---|---|
| | Capsaicin | Dihydrocapsaicin | Total |
| CYS50 | 414.02 ± 4.39$^g$ | 195.31 ± 2.09$^g$ | 609.33 ± 6.48$^f$ |
| CYS75 | 565.15 ± 3.12$^j$ | 236.00 ± 1.41$^j$ | 801.15 ± 4.51$^i$ |
| CYS100 | 631.72 ± 4.06$^l$ | 244.01 ± 1.40$^k$ | 875.73 ± 5.46$^j$ |
| CYM0 | 185.87 ± 1.33$^b$ | 130.46 ± 1.17$^b$ | 316.33 ± 2.49$^b$ |
| CYM25 | 302.57 ± 4.25$^d$ | 161.91 ± 2.40$^d$ | 464.48 ± 6.64$^d$ |
| CYM50 | 385.37 ± 7.84$^f$ | 179.76 ± 3.94$^f$ | 565.14 ± 11.77$^e$ |
| CYM75 | 498.89 ± 7.12$^i$ | 207.70 ± 3.20$^h$ | 706.60 ± 10.31$^h$ |
| CYM100 | 588.18 ± 29.57$^k$ | 226.51 ± 11.42$^i$ | 814.69 ± 40.99$^i$ |
| CYL0 | 168.48 ± 3.76$^a$ | 118.23 ± 2.72$^a$ | 286.71 ± 6.48$^a$ |
| CYL25 | 250.90 ± 7.17$^c$ | 135.23 ± 4.56$^b$ | 386.13 ± 11.73$^c$ |
| CYL50 | 327.05 ± 3.93$^e$ | 150.62 ± 2.02$^c$ | 477.68 ± 5.95$^d$ |
| CYL75 | 415.97 ± 5.39$^g$ | 172.34 ± 2.10$^e$ | 588.31 ± 7.49$^f$ |
| CYL100 | 480.69 ± 9.65$^h$ | 183.57 ± 3.72$^f$ | 664.26 ± 13.37$^g$ |

* The superscript in the table above is the result of duncan's test.

Referring to Table 1, it can be seen that even if the ratio of Cheongyang red pepper is the same, the pungency decreases when the particles are large. For example, the total capsaicinoid contents of CYS50, CYM50 and CYL50 were 609.33, 565.14 and 477.68 mg/kg, respectively, and CYS100, CYM100 and CYL100 were 875.73, 814.69 and 664.26 mg/kg, respectively, and thus, it can be seen that the lower the particle size of the red pepper powder, the higher the capsinoid content. The present invention may estimate the pungency using a spectroscopic analysis model considering the change in pungency according to the difference in this particle size.

On the one hand, according to another embodiment of the present invention, the spicy level may be corrected based on the moisture content instead of the particle size. As the particle size increases, the moisture content increases, and thus, the spicy level may be corrected accordingly. The analysis model for estimating the spicy level may include particle size or moisture content data in addition to spectroscopic image data of red pepper powder as input variables, and in some cases may further include variables such as the production area and harvest time of red pepper powder.

According to another embodiment of the present invention, instead of calculating the second spicy level by correcting the first spicy level in the spectroscopic analysis model, the second spicy level may be directly calculated by omitting the process of calculating the first spicy level and considering at least one of the pre-estimated particle size or moisture content, and the spectroscopic image data. That is, accurate spicy level may be calculated by considering particle size or moisture content in addition to spectroscopic image data as factors that affect the calculation of the spicy level.

Figure 8A:
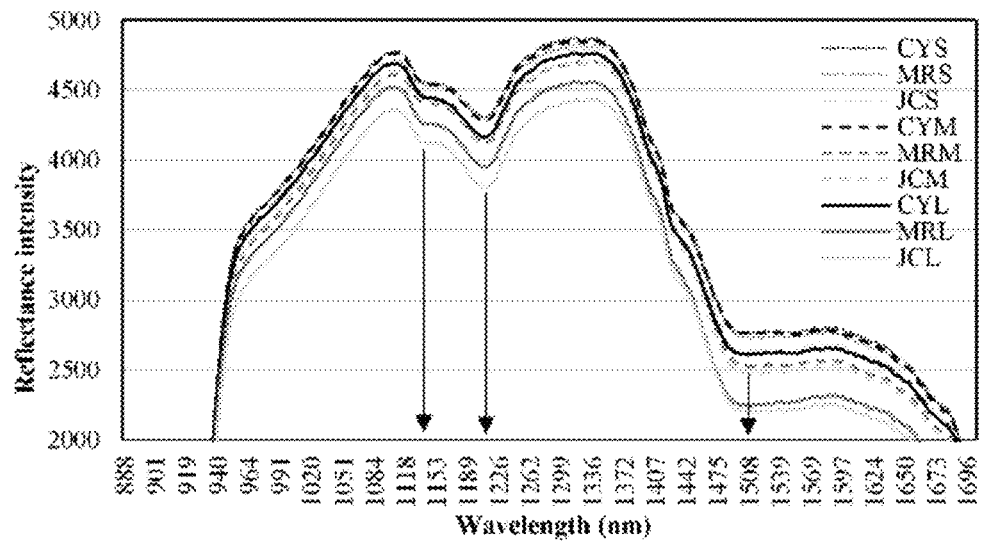
In FIG. 8A shows hyperspectral spectrum data according to the particle size and spicy level of red pepper powder analyzed by the monitoring device according to one embodiment of the present invention.
Figure 8B:
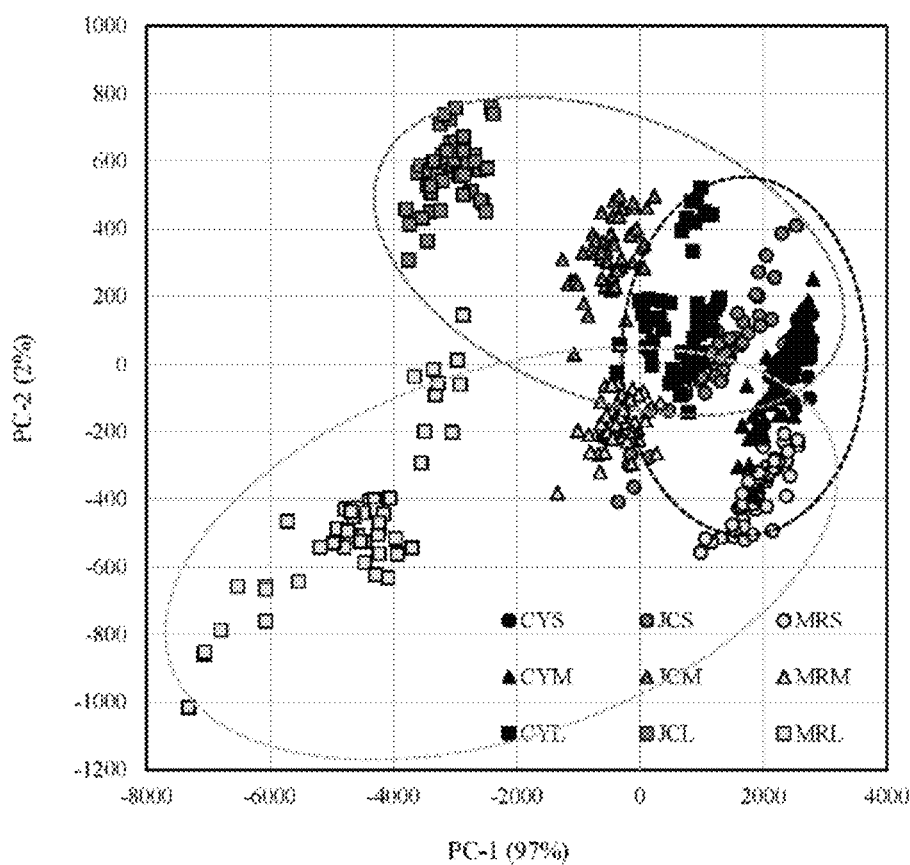
FIG. 8B-8C are diagrams showing a PCA plot.
Figure 8C:
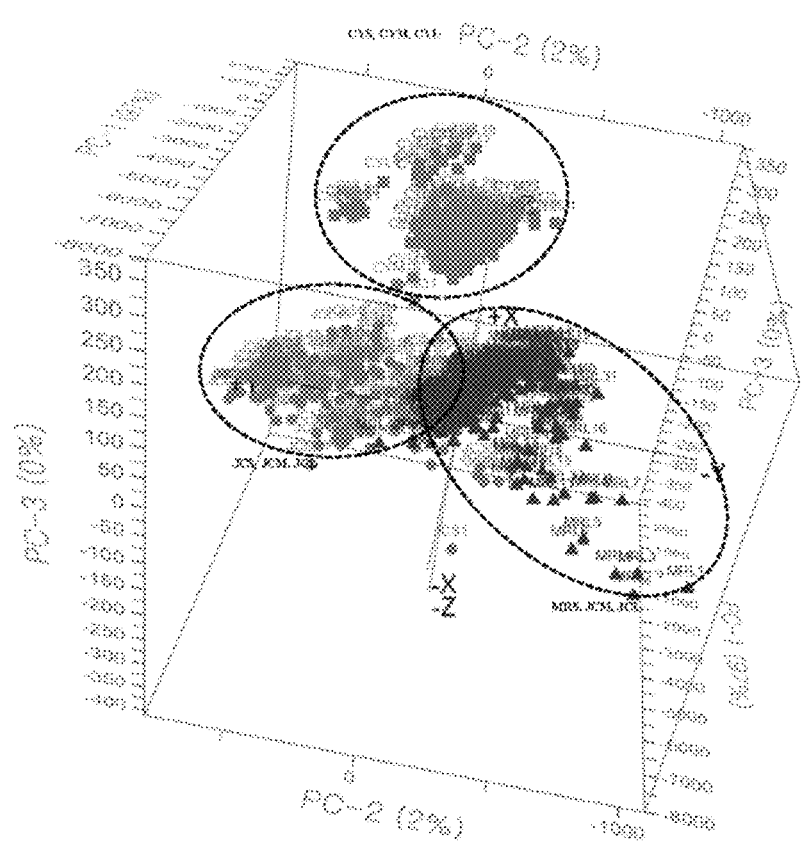

In FIGS. 8A-8C, FIG. 8A shows hyperspectral spectrum data according to the particle size and spicy level of red pepper powder, and FIG. 8B-8C show a PCA plot. In FIG. 8A, each of CY, MR and JC indicates the production area of the red pepper powder, and each of -S, -M and -L indicates the particle size. For example, CYL refers to red pepper powder with a large particle size, produced from the CY area, and CYS refers to red pepper powder with a fine particle size, produced from the CY area. From FIG. 8A, it can be seen that the absorption bands are mainly about 1120, 1220, and 1510 nm, and the stronger the pungency, the higher the reflection intensity at 1490-1600 nm. FIG. 8B-8C respectively show the results of the principal component analysis in two-dimensional and three-dimensional score plots, and it can be seen that in the two-dimensional plot, the smaller particles are clustered in the positive direction, whereas in the three-dimensional plot, it is grouped into three levels (for example, mild (0.5-1.5 level), normal spicy (1.5-2.5 level) and spicy (2.5-3.5 level) according to the degree of spiciness regardless of the particle size. From these analysis results, an analysis model capable of correcting or estimating an accurate spicy level may be created.

Figure 9:
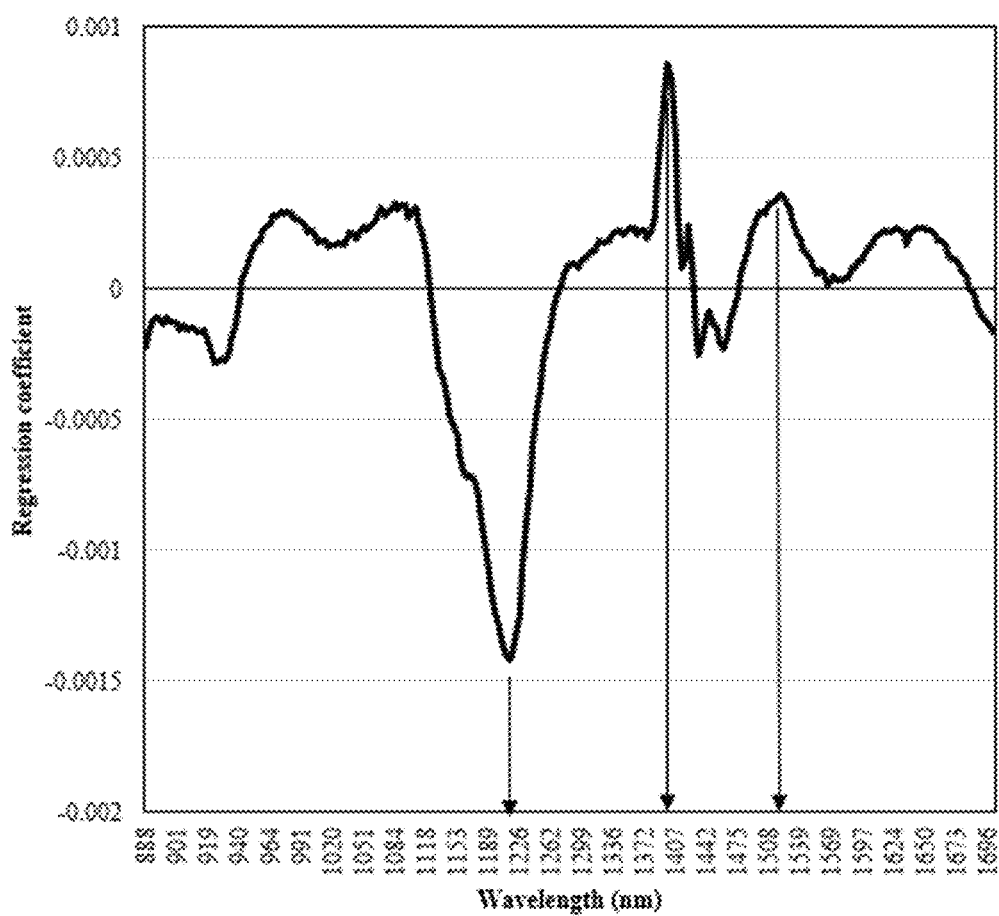
FIG. 9 is a diagram showing regression coefficients derived from the analytical results of PLS-DA in the spectrum in the full wave band (900-1700 nm) of SWIR for spicy level estimation analyzed by the monitoring device according to one embodiment of the present invention.

FIG. 9 shows regression coefficients derived from the analytical results of PLS-DA in the spectrum in the full wave band (900-1700 nm) of SWIR for spicy level estimation. Referring to FIG. 9, it can be seen that the 1201-1226 nm region, 1387-1411 nm region and 1508-1529 nm region, including 1214, 1399 and 1518 nm are optimal wavelength discrimination bands, and when the spectroscopic data is processed in the spectroscopic analysis model, the quality of red pepper powder may be discriminated based on the data of the optimum wavelength discrimination band instead of the data of the full wave band. From the above, the data processing speed or burden may be reduced. Capsaicin and dihydrocapsaicin are alkaloids with molecular formulas $C_{18}H_{27}NO_3$ and $C_{18}H_{29}NO_3$, respectively, and these consist of an aromatic ring, an amide linkage and a hydrophobic side chain. The 1st overtone stretching of the OH group and the 1st overtone stretching of the N—H group are read in the 395-1452 nm and 1520 nm wavelength bands, respectively, and the 2nd overtone is caused by the presence of a hydroxyl group (—OH) and is derived from several antioxidants in red pepper, such as capsanthin and capsaicin.

Figure 10:
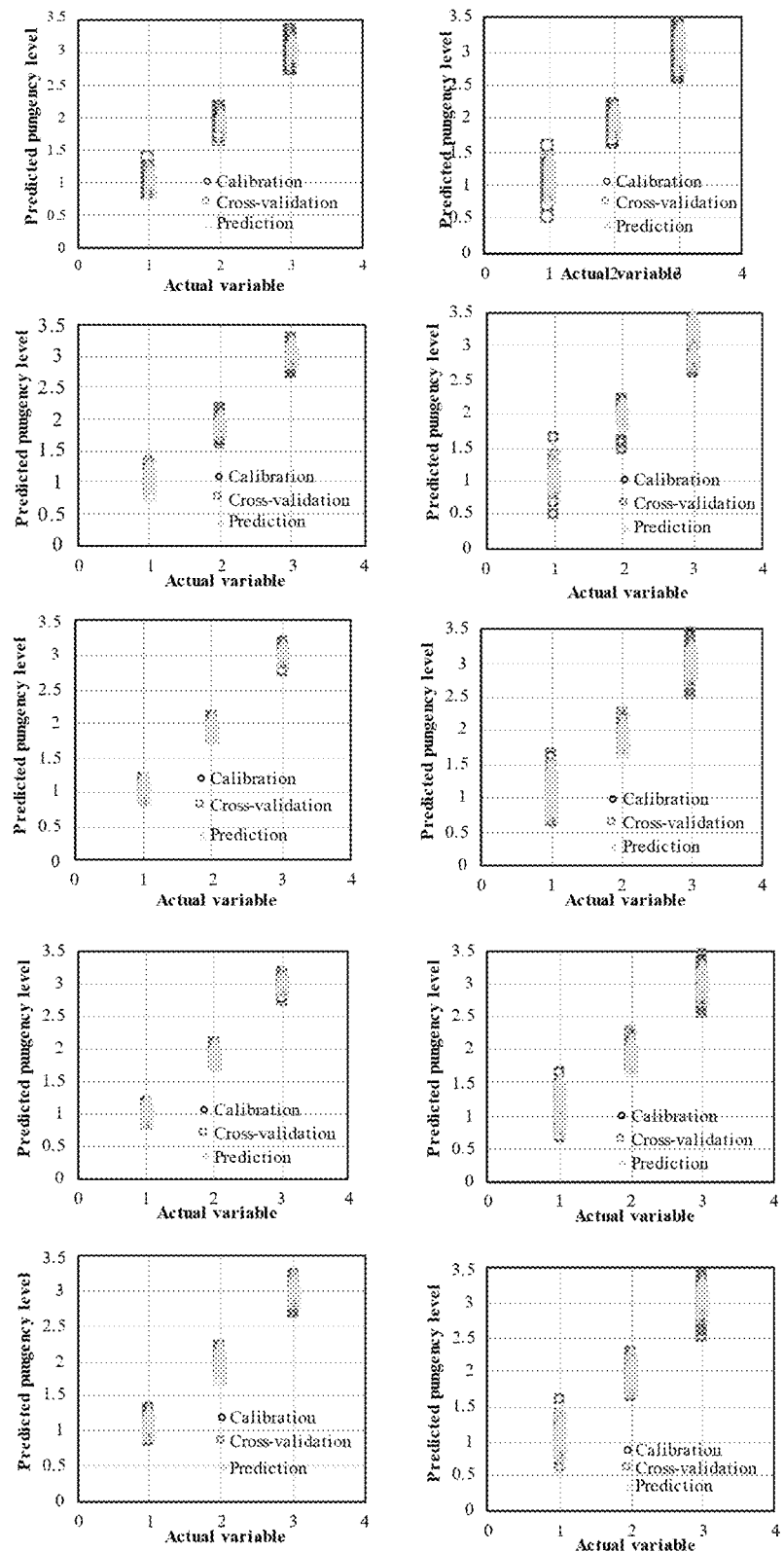
FIG. 10 is a diagram showing result values of spicy level estimation modeling of a spectroscopic analysis model according to one embodiment of the present invention.

FIG. 10 is a diagram showing result values of spicy level estimation modeling of a spectroscopic analysis model according to one embodiment of the present invention. In FIG. 10, left figures show the modeling result of the developed spicy level discrimination model (PLS-DA) in the full wave band, and right figures show the modeling result of the developed spicy level discrimination model (PLS-DA) in the optimal wavelength discrimination band (for example, 1201-1226 nm region, 1387-1411 nm region and 1508-1529 nm region, including 1214, 1399 and 1518 nm). In addition, the result values of the predictive model according to preprocessing such as raw data, normalization, SNV, MSC and SG are shown in order from the top. In FIG. 10, the pungency was classified into three levels as follows: 1, mild; 2, normal spicy; and 3, spicy.

Referring to FIG. 10, according to the spectroscopic analysis model according to one embodiment of the present invention, pungency prediction was successfully performed in all preprocessing models including raw data, and in particular, SNV and MSC preprocessing models were analyzed to have high predictive performance. In addition, there is no significant difference in performance between the analytical results based on data of all wavelength bands and the analytical results based on the data of specific wavelength bands selected as the optimal wavelength discrimination bands, and thus, it can be seen that sufficient performance may be guaranteed with only the data of specific wavelength bands.

Through the above-described processes, the monitoring device 100 estimates and calculates a first particle size and/or a first moisture content, a first spicy level and/or a second spicy level based on the spectroscopic image data periodically or intermittently received from the spectroscopic device 10, and stores the data in the memory 120. In addition, it may predict the quality of red pepper powder to be mixed and discharged in the mixer 240 in the same batch, for example, a third spicy level (final spicy level), a second particle size (final particle size), a second moisture content (final moisture content), a second sugar content (final sugar content) or a second ASTA value (final ASTA value) based on the data stored in the memory 120.

The mixer 240 is disposed at the rear end of the red pepper powder manufacturing process, so that the red pepper powder that has undergone the grinding process, filtration process and sterilization process may be finally blended in the mixer 240. In this case, the mixer 240 operates only when a certain amount of red pepper powder to be mixed is filled.

In the present invention, in order to calculate the quality of the first mixed red pepper powder to be put into and blended into the mixer 240 in the same batch and produced as red pepper powder of the same quality, for example, a third spicy level, a second particle size, a second moisture content, a second sugar content or a second ASTA value, data of the first particle size, the first moisture content, the second spicy level, the first sugar content or the first ASTA value and the input amount (production amount) of red pepper powder corresponding thereto pre-stored in the memory 120 may be used. For example, if the measurement is made by the spectroscopic device 10 five times every 30 minutes, and the input amount (production amount) of each red pepper powder was 10 kg, 8 kg, 10 kg, 9 kg and 10 kg, the predicted value of each quality is multiplied by the input amount of red pepper powder, so that a third spicy level, the final particle size (second particle size), the final moisture content (second moisture content), and the final sugar content (second sugar content) or the final ASTA value (second ASTA value) of the final red pepper powder (first mixed red pepper powder) may be calculated.

In addition, in the present invention, the second spicy level corresponds to a value corrected or calculated in consideration of particle size or moisture content, respectively, but since red pepper powder having a different particle size distribution is mixed in the mixer 240, the second particle size may also be taken into account when calculating the final spicy level (i.e., third spicy level) of the first mixed red pepper powder. Accordingly, according to the present invention, the quality (for example, spicy level, particle size, and the like) of the first mixed red pepper powder may be pre-estimated before mixing in the mixer 240.

Information on the target quality of the first mixed red pepper powder, for example, target spicy level, target particle size, target sugar content or target ASTA value, may be set by the user or pre-stored in the memory 120. The monitoring device 100 (processor) may compare the quality data (for example, target spicy level, target particle size, target sugar content or target ASTA value) corresponding to the target reference value set by the user or stored in the memory 120 with the calculated quality data (for example, third spicy level, second particle size, second sugar content or second ASTA value) of the first mixed red pepper powder to determine at least one of the type, input amount, moisture content and grinding degree of dried red pepper to be added to the future grinding process, or to determine at least one of the type (spicy level), input amount, moisture content and particle size of red pepper powder to be added to the mixer 240 in the future, in order to achieve the target standard value.

In this case, the target quality (for example, spicy level, particle size, moisture content, ASTA value, and the like) may be set as a numerical value or a level (or step) having a certain numerical range, and similarly, the quality data calculated or predicted by the monitoring device 100, for example, spicy level (first spicy level, second spicy level and third spicy level), particle size (first particle size and second particle size), and the like may be also calculated as numerical values or levels.

In this case, the type of dried red pepper refers to the type according to classification by quality, such as spicy level (for example, spicy red pepper powder, normal spicy red pepper powder, mild spicy red pepper powder, and the like), degree of drying, and the like, and the griding degree corresponds to process control values in the grinder 210, such as coarse crushing or crushing degree, crushing method, grinding strength and crushing time. If the manufacturing process system 200 includes a dried pepper production system, for example, a drying process, the monitoring device 100 may calculate control values of the drying process, such as drying time, drying intensity, drying temperature, and the like to control the manufacturing process system 200.

If the calculated quality (for example, third spicy level, second particle size, second moisture content or second ASTA value) matches the target reference value of each quality (for example, target spicy level, target particle size, target sugar content or target ASTA value) or belongs to the corresponding level, the monitoring device 100 may display on the display part a message that the mixer 240 may blend the filtered and sterilized red pepper powder in the meantime without any special measures.

On the other hand, if any one of the calculated qualities (for example, third spicy level, second particle size, second moisture content or second ASTA value) does not match or does not belong to the target reference value of quality, the monitoring device 100 calculates at least one of the type (spicy level and the like), input amount, moisture content and grinding degree (crushing degree) of dried red pepper to be added to the future crushing process, in order to ensure that the quality of the first mixed red pepper powder matches the target reference value of quality or belongs to the target level. For example, in order to manufacture 15 kg of red pepper powder having a target spicy level of level 3, if the third spicy level of 10 kg of the first mixed red pepper powder to be added to the mixer 240 is currently predicted to be level 2.5, it may be decided to introduce 5 kg of dried red pepper having a spicy level of level 4 into the grinder 210. As another example, in order to manufacture 15 kg of red pepper powder having a target spicy level of level 3, if the third spicy level of 10 kg of the first mixed red pepper powder to be added to the mixer 240 is currently predicted to be level 2.5, it may be decided to introduce 5 kg of dried red pepper having a spicy level of level 4 into the grinder 210.

In another embodiment, at least one of the type (for example, spicy level and the like), input amount, moisture content and particle size of the second red pepper powder to be additionally added to the mixer 240 may be also determined. For example, if the target spicy level is level 3 and the third spicy level of 10 kg of the first mixed red pepper powder to be mixed to the mixer 240 is currently predicted to be level 2.5, it may be decided to additionally introduce 5 kg of red pepper powder having a spicy level of level 4 into the mixer 240. As another example, if the target particle size is level 2 and the particle size of 10 kg of the first mixed red pepper powder to be mixed to the mixer 240 is currently estimated to be level 3, it may be decided to introduce 5 kg of red pepper powder having a particle size of level 1 into the mixer 240.

The monitoring device 100 makes it possible to manufacture red pepper powder having a desired target level of particle size and spicy level, by analyzing the spectroscopic image data of red pepper powder transmitted periodically or intermittently from the spectroscopic device 10 to store the calculated quality (for example, first particle size, first moisture content, and the spicy level and/or second spicy level) data of red pepper powder in the memory 120 together with the corresponding production amount of red pepper powder to be manufacture, predicting the third spicy level and second particle size of the first mixed red pepper powder to be produced in the future after the produced red pepper powder is gathered and added to the mixer 240, based on these quality data, and if the predicted values are outside the quality target, determining the quality (for example, spicy level, particle size, moisture content, sugar content, ASTA value, and the like) and amount of the dried red pepper to be added to the grinder 210 or the red pepper powder to be added to the mixer 240, thereby controlling the process control value or additionally adding dried red pepper or red pepper powder of the corresponding quality.

In this way, according to the present invention, not only may red pepper powder of a desired quality be produced, but also red pepper powder that meets specifications may be produced, by monitoring the quality of red pepper powder currently being produced in the red pepper powder manufacturing process and determining the quality or process control value of dried red pepper or red pepper powder to be introduced into the grinder 210 or mixer 240 in the future in order to produce red pepper powder that matches the target quality of red pepper powder.

Figure 11:
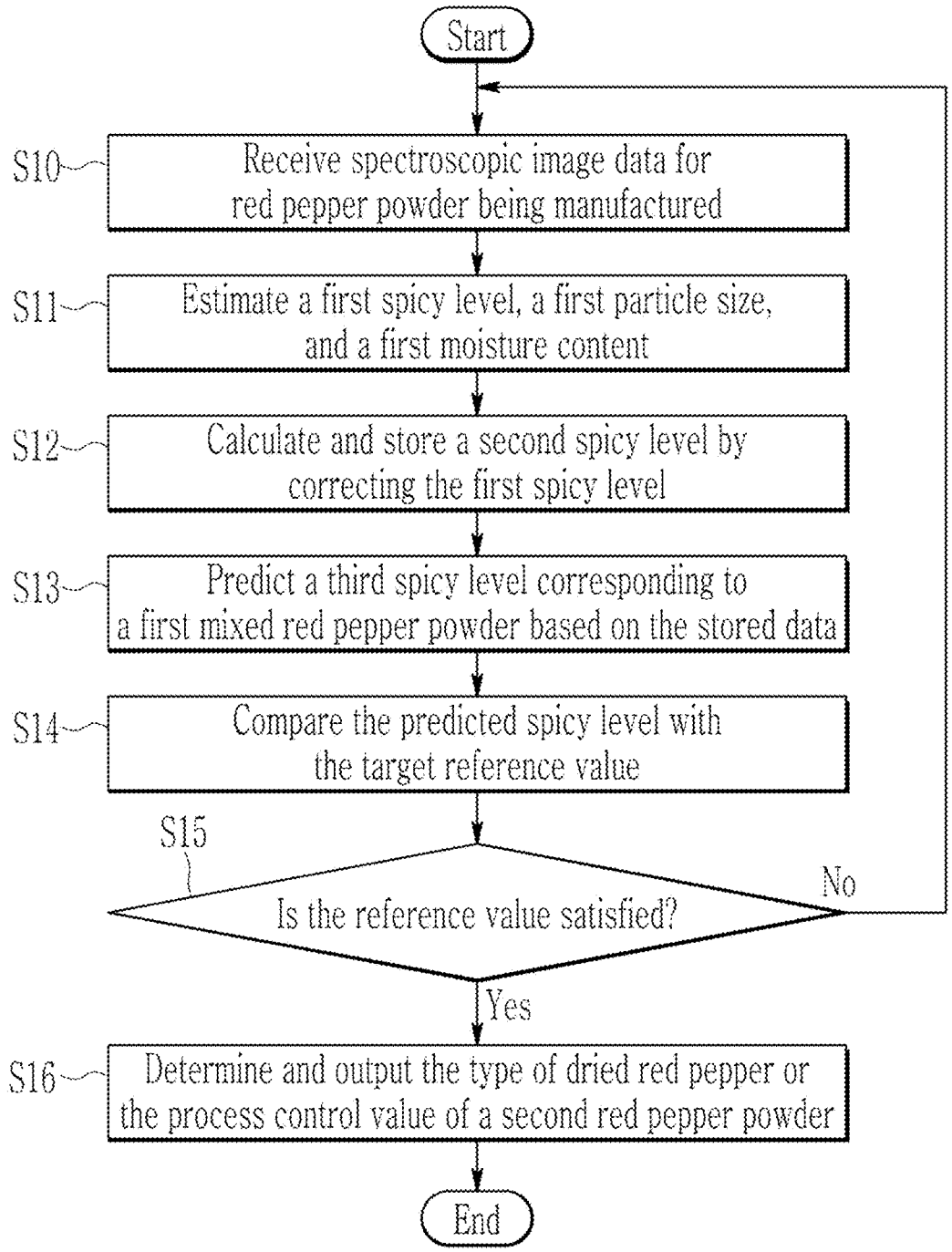
FIG. 11 is a flowchart of a method for monitoring the quality of red pepper powder by the monitoring device according to one embodiment of the present invention.

A method for monitoring the quality of red pepper powder by the monitoring device 100 according to one embodiment of the present invention will be described with reference to FIG. 11. FIG. 11 is a flowchart of a method for monitoring the quality of red pepper powder by the monitoring device 100 according to one embodiment of the present invention.

The spectroscopic device 10 is installed in or before and after at least one of the grinding process, filtration process and sterilization process of red pepper powder to periodically or intermittently obtain spectroscopic image data of the red pepper powder and transmits the data to the monitoring device 100. The monitoring device 100 receives the spectroscopic image data of red pepper powder in the manufacturing process from the spectroscopic device 10 (S10).

The monitoring device 100 estimates the quality of red pepper powder, for example, at least one of a first particle size and a first moisture content, and a first spicy level, based on the received spectroscopic image data (S11). As described above, since the spicy level is affected by the particle size and the moisture content, the particle size or the moisture content is considered in estimating the spicy level. The monitoring device 100 calculates a second spicy level by correcting the first spicy level based on the first particle size or the first moisture content, and stores it in the memory 120 (S12). As described above, the first spicy level may be calculated in consideration of the particle size or moisture content, rather than the method of correcting the spicy level.

On the one hand, the amount of red pepper powder produced in response to the measurement is automatically calculated or stored in the memory 120 by the user's input. For example, if a spectroscopic image of red pepper powder is obtained at 30 minute intervals and the amount of red pepper powder normally produced for 30 minutes is 20 kg, the measurement time, spectroscopic image, first particle size, first moisture content, first spicy level or second spicy level and production amount (20 kg) are recorded in the memory 120, and these data are recorded every 30 minutes. As described above, the first sugar content and the first ASTA value of red pepper powder may be additionally estimated and stored.

The monitoring device 100 may calculate the quality, for example, third spicy level, second particle size, second moisture content, and further second sugar content or second ASTA value, of the first mixed red pepper powder to be added to the mixer 240 and be produced in the future, based on the data recorded in the memory 120 (S13). Whenever spectroscopic image data is transmitted and analyzed from the spectroscopic device 10, the predicted value for the quality of the first mixed red pepper powder is updated.

The monitoring device 100 may compare the predicted quality of the red pepper powder with the target reference value (S14), and if the target reference value is not satisfied (S15), it may determine the quality or process control value, and amount of red pepper powder of the dried red pepper to be added to the grinder 210 or the red pepper powder to be added to the mixer 240 in the future to control the red pepper powder manufacturing process based on this (S16).

In this way, according to the present invention, red pepper powder of a desired quality be produced, by continuously monitoring the quality of red pepper powder currently being produced in the red pepper powder manufacturing process to predict the quality of the red pepper powder to be produced, and determining the quality or process control value of dried red pepper or red pepper powder to be introduced into the grinder 210 or mixer 240 in the future in order to produce red pepper powder that matches the target quality of red pepper powder.

The above-described device and its control may be implemented in a hardware component, a software component, and/or a combination of the hardware component and the software component. For example, the device and component as described in embodiments may be implemented using one or more general-purpose computers or special-purpose computers, such as a processor, a controller, an arithmetic logic unit (ALU), a digital signal processor, a microcomputer, a field programmable gate array (FPGA), a programmable logic unit (PLU), a microprocessor, or any other device capable of executing and responding to instructions. The processing device may execute an operating system (OS) and one or more software applications running on the operating system. In addition, the processing device may access, store, manipulate, process, and generate data in response to the execution of the software. For the convenience of understanding, although the processing device may be described as one being used, those of ordinary skill in the art will appreciate that the processing device may comprise a plurality of processing elements and/or a plurality of types of processing elements. For example, the processing device may include a plurality of processors or one processor and one controller. In addition, other processing configurations such as a parallel processor are possible.

The software may include a computer program, code, instructions, or a combination of one or more of these, and may configure the processing device to operate as desired or may instruct the processing device independently or collectively. The software and/or data may be permanently or temporarily embodied in any type of machine, component, physical device, virtual equipment, computer storage medium or device, in order to be interpreted by the processing device or to provide instructions or data to the processing device. The software may be distributed over networked computer systems and stored or executed in a distributed manner. The software and data may be stored on one or more computer-readable recording media.

The method according to one embodiment may be embodied in the form of program instructions, which may be executed through various computer means, and recorded on a computer-readable medium. The computer readable medium may include program instructions, data files, data structures, and the like, alone or in combination. The program instructions recorded on the media may be those specially designed and configured for one embodiment, or those that are well known and available to one of ordinary skill in the computer software art. Examples of computer-readable recording media include a magnetic media such as a hard disk, a floppy disks, and a magnetic tape, an optical media such as CD-ROM and DVD, magneto-optical media such as a floptical disk, and a hardware device specifically configured to store and execute program instructions, such as ROM, RAM, a flash memory, and the like. Examples of program instructions include not only machine language codes such as those generated by a compiler, but also high-level language codes that can be executed by a computer using an interpreter, or the like. The hardware device as described above may be configured to operate as one or more software modules to perform the operations of one embodiment, and vice versa.

Although embodiments has been described by a limited embodiment and the drawings as described above, those of skill in the art will appreciate that various modifications and alterations may be made from the description above. For example, although the techniques as described herein is performed in a different order than the methods as described herein, and/or components such as the systems, structures, devices, circuits, and the like as described herein are joined or combined in a different form than the method as described herein, or replaced or substituted by other components or equivalents, appropriate results may be achieved.

Therefore, other implementations, other embodiments, and equivalents of the claims are within the scope of the appended claims.

DESCRIPTION OF SYMBOLS

| | |
|---|---|
| 10: Spectroscopic device | 100: Monitoring device |
| 110: Processor | 120: Memory |
| 130: DB | 140: Communication interface |
| 150: Input and output interface | 160: Input and output device |
| 200: Manufacturing process system | 210: Grinder |
| 220: Filter | 230: Sterilizer |
| 240: Mixer | 300: Network |
| 400: User terminal (control part) | |

The invention claimed is:

1. A method for monitoring the quality of red pepper powder, comprising the steps of:
estimating at least one of a first particle size and a first moisture content of a first red pepper powder, based on the spectroscopic image data of the first red pepper powder obtained in or before and after at least one of the grinding process, filtration process and sterilization process of red pepper powder;
calculating a second spicy level, based on at least one of the first particle size and the first moisture content, and the spectroscopic image data; and
estimating a third spicy level of a first mixed red pepper powder in the mixing process, based on at least one of the first particle size and the first moisture content, the second spicy level, and an input amount of the first red pepper powder.

2. The method for monitoring the quality of red pepper powder according to claim 1, further comprising the step of estimating a first spicy level of the first red pepper powder, based on the spectroscopic image data,
wherein the second spicy level is calculated by correcting the first spicy level based on at least one of the first particle size and the first moisture content.

3. The method for monitoring the quality of red pepper powder according to claim 1, further comprising the step of estimating at least one of a second particle size and a second moisture content of the first mixed red pepper powder, based on at least one of the first particle size and the first moisture content, and the input amount of the first red pepper powder.

4. The method for monitoring the quality of red pepper powder according to claim 3, further comprising the step of comparing the pre-set target spicy level and target particle size of the first mixed red pepper powder with the third spicy level and the second particle size to determine at least one of the type, input amount, moisture content and grinding degree of dried red pepper to be added to the future grinding process, or to determine at least one of the spicy level, input amount, moisture content and particle size of a second red pepper powder to be added to the future mixing process.

5. The method for monitoring the quality of red pepper powder according to claim 1, further comprising the steps of:
estimating a first sugar content of the first red pepper powder based on the spectroscopic image data;
estimating a second sugar content of the first mixed red pepper powder; and
comparing the pre-set target sugar content of the first mixed red pepper powder with the second sugar content to determine the type or input amount of dried red pepper to be added to the future grinding process, or to determine the sugar content or input amount of the second red pepper powder to be added to the future mixing process.

6. The method for monitoring the quality of red pepper powder according to claim 1, further comprising the steps of:
estimating a first ASTA value of the first red pepper powder based on the spectroscopic image data;
estimating a second ASTA value of the first mixed red pepper powder; and
comparing the pre-set target ASTA value of the first mixed red pepper powder with the second ASTA value to determine the type or input amount of dried red pepper to be added to the future grinding process, or to determine the ASTA value or input amount of the second red pepper powder to be added to the future mixing process.

7. The method for monitoring the quality of red pepper powder according to claim 3, further comprising the step of generating a visualization map for the first particle size, the first moisture content, the second particle size, the second moisture content, the second spicy level, and the third spicy level.

8. The method for monitoring the quality of red pepper powder according to claim 1, further comprising the step of storing the estimated or determined data of the first red pepper powder, the second red pepper powder and the first mixed red pepper powder in a memory, or sending and receiving the data to the control part.

9. A computer program stored on a non-transitory recording medium comprising instructions, wherein the instructions are configured to cause a processor to perform the method according to claim 1.

10. The computer program stored on a non-transitory recording medium according to claim 9, configured to further perform the step of storing the estimated or determined data of the first red pepper powder, the second red pepper powder and the first mixed red pepper powder in a memory, or sending and receiving the data to the control part.

11. A system for monitoring the quality of red pepper powder, comprising:
   one or more spectroscopic devices configured to obtain spectroscopic image data of a first red pepper powder in or before and after at least one of the grinding process, filtration process and sterilization process of red pepper powder; and
   a monitoring device configured to receive spectroscopic image data from the spectroscopic devices,
   wherein the monitoring device is configured to perform the method according to claim 1.

12. The system for monitoring the quality of red pepper powder according to claim 11, wherein the spectroscopic devices are configured to periodically or intermittently obtain spectroscopic image data of the first red pepper powder.

13. The system for monitoring the quality of red pepper powder according to claim 11, wherein the monitoring device is configured to store the estimated or determined data of the first red pepper powder, the second red pepper powder and the first mixed red pepper powder in a memory, or to send and receive the data to the control part.

* * * * *